(12) United States Patent
Ziegner

(10) Patent No.: US 9,381,294 B2
(45) Date of Patent: Jul. 5, 2016

(54) AUTO-INJECTOR CASE

(71) Applicant: Ulrike H. M. Ziegner, Palos Verdes Estates, CA (US)

(72) Inventor: Ulrike H. M. Ziegner, Palos Verdes Estates, CA (US)

(*) Notice: Subject to any disclaimer, the term of this patent is extended or adjusted under 35 U.S.C. 154(b) by 12 days.

(21) Appl. No.: 13/920,019

(22) Filed: Jun. 17, 2013

(65) Prior Publication Data

US 2014/0367288 A1  Dec. 18, 2014

(51) Int. Cl.
*A61J 1/16* (2006.01)
*A61M 5/00* (2006.01)
*F25D 3/08* (2006.01)
*A61M 5/20* (2006.01)

(52) U.S. Cl.
CPC .............. *A61M 5/002* (2013.01); *A61M 5/20* (2013.01); *F25D 3/08* (2013.01)

(58) Field of Classification Search
CPC ........... A61M 5/002; A61M 5/20; A61J 1/16; F25D 3/08
USPC ......... 206/366, 364, 365, 804, 250, 249, 438, 206/571, 305
See application file for complete search history.

(56) References Cited

U.S. PATENT DOCUMENTS

| | | | | |
|---|---|---|---|---|
| 2,093,537 A * | 9/1937 | Balint | 206/571 |
| 2,283,599 A * | 5/1942 | Dickinson | 206/306 |
| 2,740,516 A * | 4/1956 | Renn | 206/229 |
| 3,621,994 A * | 11/1971 | Brown | 206/446 |
| 4,119,248 A * | 10/1978 | Butler et al. | 224/148.3 |
| 4,214,658 A * | 7/1980 | Crow | 206/244 |
| 4,240,547 A * | 12/1980 | Taylor | 206/204 |
| 4,250,998 A * | 2/1981 | Taylor | 206/570 |
| 4,446,970 A * | 5/1984 | Further | 206/569 |
| 4,501,360 A * | 2/1985 | Levy et al. | 206/443 |
| 4,738,364 A * | 4/1988 | Yeager | 206/563 |
| 4,872,563 A * | 10/1989 | Warder et al. | 53/471 |
| 4,932,533 A * | 6/1990 | Collier | 206/569 |
| 5,029,699 A * | 7/1991 | Insley et al. | 206/204 |
| 5,069,336 A * | 12/1991 | Mauthe | 206/219 |
| D338,727 S * | 8/1993 | Rand et al. | D24/121 |
| 5,415,282 A * | 5/1995 | Kienholz | 206/216 |
| 6,003,666 A * | 12/1999 | Dougherty | 206/204 |
| 6,595,362 B2 * | 7/2003 | Penney et al. | 206/364 |
| 8,096,414 B2 * | 1/2012 | Finnestad et al. | 206/366 |
| 2002/0050462 A1 * | 5/2002 | Penney et al. | 206/363 |
| 2006/0169611 A1 * | 8/2006 | Prindle | 206/364 |
| 2007/0119743 A1 * | 5/2007 | Tucker et al. | 206/503 |
| 2007/0125677 A1 * | 6/2007 | Oronsky et al. | 206/446 |
| 2007/0284278 A1 * | 12/2007 | Langone | 206/528 |
| 2009/0179053 A1 * | 7/2009 | Cooney et al. | 224/219 |
| 2011/0210021 A1 * | 9/2011 | Logel et al. | 206/223 |
| 2013/0068641 A1 * | 3/2013 | Puglisi | 206/232 |

* cited by examiner

*Primary Examiner* — Steven A. Reynolds

(74) *Attorney, Agent, or Firm* — Lewis Brisbois LLP; Jon Hokanson

(57) ABSTRACT

An insulated, epinephrine auto-injector case that also includes a rapid-opening cap, two spring-loaded chambers, each with a rapid-opening cap to facilitate immediate and easy availability of the auto-injector for grasping by the user.

17 Claims, 3 Drawing Sheets

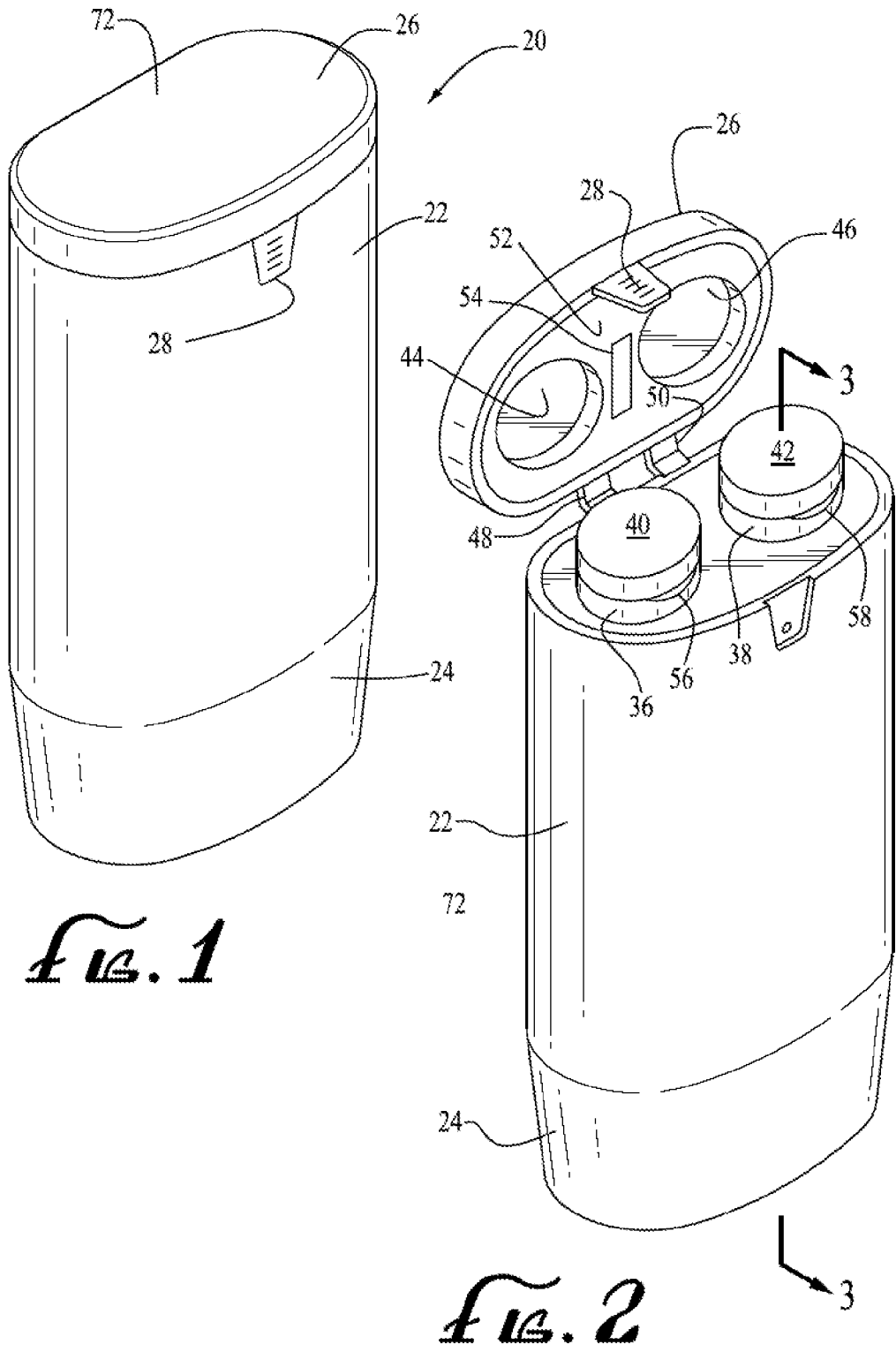

AUTO-INJECTOR CASE

CROSS REFERENCE TO RELATED APPLICATION

This application claims the benefit of U.S. application 61/660,760, filed Jun. 17, 2012, and which is incorporated by reference herein.

FIELD OF INVENTION

The invention relates generally to cases for medication delivery devices such as auto-injectors used for injection of epinephrine.

BACKGROUND

Cases for medication delivery devices such as auto-injectors used for injection of epinephrine are well-known. However, no known conventional epinephrine auto-injector case provides an insulated chamber that protects the epinephrine from degradation by extreme or prolonged temperature variance from ambient temperature. Also, no known conventional epinephrine auto-injector case provides a spring-loaded, internal container or chamber that forces the contained auto-ejector immediately upon opening an internal, rapid-release cap. Also, no known epinephrine auto-injector case provides for sensing and recording the temperature inside of the case to provide information on degradation or loss of effectiveness of the encased epinephrine due to prolonged storage in high temperature environments.

SUMMARY

The auto-injector cases according to the present invention overcome the drawbacks of known auto-injector cases by providing a spring-loaded and/or insulated chambers for two injectors to facilitate rapid availability of each injector for grasping by the user, and a pop-open cap to provide secure containment of each injector within an insulated, protective case. Preferably the cap is of a design that provides for rapid access to the injector, and preferably the case is sized and configured to house two injectors, although it may also be adapted for a single injector. In another preferred embodiment a temperature measuring device or strip of material is included on the interior of the case to monitor and record the temperature inside of the case so that the user can be informed if the injector has been heated to a degree that renders its epinephrine of reduced effectiveness or ineffective.

Several embodiments, features, aspects, and advantages of the invention will become better understood with regard to the following description, appended claims and accompanying drawings.

BRIEF DESCRIPTION OF THE DRAWINGS

The foregoing aspects and the attendant advantages of the present invention will become more readily appreciated by reference to the following detailed description, when taken in conjunction with the accompanying drawings, wherein:

FIG. 1 is a front perspective view of a preferred embodiment case for a conventional EpiPen® brand epinephrine auto-injector;

FIG. 2 is a perspective view of the FIG. 1 embodiment with the case top cap open and showing a closed cap for each of two contained auto-injectors;

Figure 3:
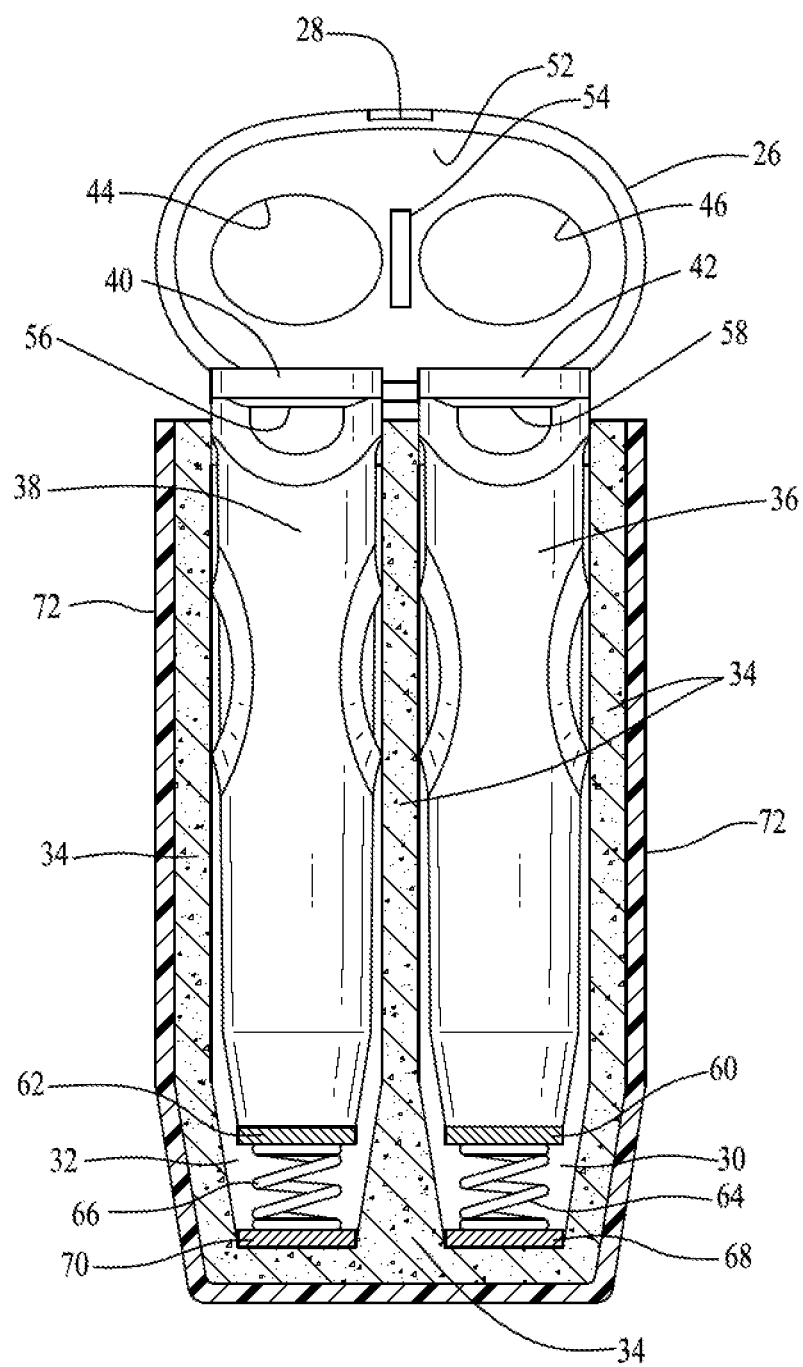
FIG. 3 is a cross-sectional view of the FIG. 1 embodiment taken through line 3-3 of FIG. 2.

Reference symbols or names are used in the Figures to indicate certain components, aspects or features shown therein. Reference symbols common to more than one Figure indicate like components, aspects or features shown therein.

DETAILED DESCRIPTION

With reference to FIGS. 1-4 preferred embodiments of cases for auto-injectors are described. Case 20 preferably is sized and adapted to hold two EpiPen® brand epinephrine auto-injectors in a side-by-side relationship. The case 20 has a main body 22, a tapered bottom part 24, and a rapid-open top cap 26 with a tab 28.

Interior containers, or alternatively, cavities 30, 32 are formed inside of the case 20. Insulation 34 surrounds the cavities 30, 32 as shown in FIG. 3 and functions to maintain the temperature of the epinephrine at room temperature for a reasonable time in elevated temperature environments. The insulation material is preferably foam insulation, such as closed cell polyurethane foam. Other materials may be used so long as it accomplishes the objective of preventing the epinephrine to be rendered useless due to elevated temperatures.

With reference to FIG. 3 two EpiPen® brand epinephrine auto-injectors 36, 38 are shown in side-by-side relationship. As shown in FIGS. and 3 each of the containers 36, 38 have a top cap 40, 42. The top caps 40, 42 fit within shallow cavities 44, 46 in the body of case top cap 26. Each of the caps 40, 42 for the individual containers also have rapid opening caps and cap tabs 56, 58. As shown in FIG. 2 the case top cap 26 has double, flexible hinges 48, 50 that join the top cap 26 to the back side of the body 22. The individual caps 40, 42 preferably have flexible hinges, of the same type as hinges 48, 50. Cavities 44, 46 are preferably formed in insulation 52, which in turn is positioned in top cap 26.

A conventional temperature measuring strip 54 is placed inside of the case, preferably on the underside of the top cap 26 and on the insulation 52. The temperature measuring strip functions to monitor the temperature inside of the case, which approximates the temperature of the encased epinephrine. Preferably the strip 54 is of the type that provides an indication of the highest temperature reached inside of the case, thus providing an indication on whether the epinephrine has been heated to a temperature high enough to render the epinephrine ineffective. In an alternate embodiment, single use strips are used so that a replacement strip is placed in the case upon replacement of the auto-injector.

Each individual container 36, 38 has a spring loaded bottom flange 60, 62. Springs 64, 66 are anchored to container bottom plates 68, 70. The springs 64, 66 function to cause the encased injector 36 or 38 to pop up immediately upon opening the cap 26 and facilitate grasping of either injector 36 or 38 by the user when in urgent need of an epinephrine injection.

The case 22 is preferably made of a hard material, of a predetermined thickness and its outer surface 72 (FIGS. 3 and 4) of a reflective material. In one alternate embodiment the back side of the case 20 has a belt clip. Other alternate embodiments could include loops for a shoulder strap, or other type of mounting or carrying structures such as clips, Velcro® brand fasteners.

The case housing is sized to include conventional insulation material outside of the auto-injector cavities and inside of the housing. Preferred insulation would be foam insulation, such as closed cell polyurethane foam. The volume of the space inside of the housing for the insulation in combination with the specific insulation capability of the chosen insulation material is sufficient to prevent over-heating of the contained epinephrine for sustained periods of high ambient temperatures, such as would be experienced inside of a glove compartment in an automobile during the summer in a warm climate. The amount or volume of insulation material preferably should be sufficient to maintain the encased auto-injector(s) at room temperature, that is about 65-75° F. during the daytime when the case is exposed to the sun, or in the glove compartment of a car or truck. The case 20 is made of, preferably, a hard, durable material such as ABS plastic to withstand dropping and other blunt force contacts.

Caps 40, 42 are of any conventional design, such as the type of pop-top or snap-open caps that are provided on conventional EpiPen® brand epinephrine auto-injectors.

During use an EpiPen® brand epinephrine auto-injector is placed in each of the cavities or internal containers 30, 32 and pressed downward to move the plates 60, 62 downward and compress the springs 64, 66 against the bottoms or plates 68, 70. External cap 26 is then closed over the two internal caps 40, 42. The injector-loaded case may then be carried by a user or stored in a convenient place such as a backpack, glove compartment, etc. When a need arises, such as the onset of an allergic reaction, the user can quickly open outer cap 26, and quickly retrieve one of the injectors. Upon opening top cap 26, the contained auto-injectors will pop out as the spring 64 or 66 uncoils and will present the injectors for easy grasping by the user. The user then opens the auto-injector cap and uses the auto-injector in accordance with it's and the user's doctor's instructions.

After loading and until use, the case protects the auto-injectors from physical damage and also protects the epinephrine from degradation due to heat or cold.

Figures 4, 5:
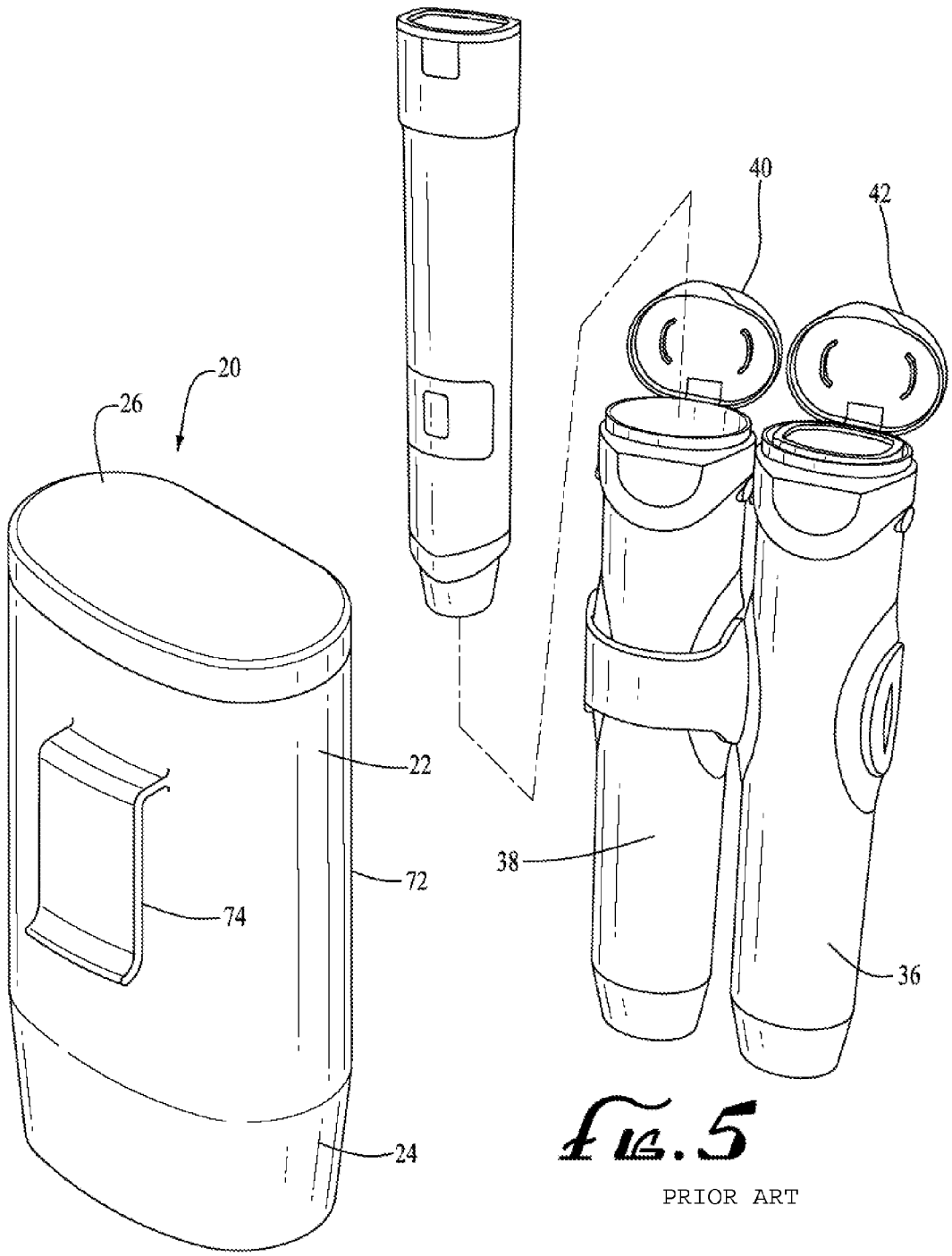
FIG. 4 is a rear perspective view of the FIG. 1 case, showing a belt clip.
FIG. 5 is a front perspective view of a conventional case and an EpiPen® brand epinephrine auto-injector showing how the injector is inserted and withdrawn from the case.

Conventional cases for EpiPen® brand epinephrine auto-injectors are known and one embodiment is shown in FIG. 5. Such cases are made of a hard plastic and are not insulated. Each case typically has a rapid opening (pop-top) cap.

Although specific embodiments of the invention have been described, various modifications, alterations, alternative constructions, and equivalents are also encompassed within the scope of the invention.

The specification and drawings are, accordingly, to be regarded in an illustrative rather than a restrictive sense. It will, however, be evident that additions, subtractions, deletions, and other modifications and changes may be made thereunto without departing from the broader spirit and scope of the invention as set forth in the claims.

What is claimed is:

1. An insulated epinephrine auto-injector system comprising:
    an epinephrine auto-injector container having a first container end and a longitudinal centerline extending from the first container end to a second container end, an epinephrine auto-injector and an auto-injector container top cap positioned adjacent the first container end;
    said auto-injector container having sides of a predetermined length from the first container end to the second container end, a predetermined outer periphery, said auto-injector container top cap is connected to the auto-injector container at the first container end by a hinge and rotatable about an axis perpendicular to the container longitudinal centerline, a closed bottom at the second container end and a cavity open at the first container end;
    said epinephrine auto-injector including an auto-injector top cap, a substantial part of said auto-injector positioned in said cavity; and,
    thermal insulation positioned between said cavity and said container outer periphery, and surrounding said auto-injector and said auto-injector top cap.

2. The auto-injector system of claim 1 further including a temperature measuring strip positioned in said system.

3. The auto-injector system of claim 1 wherein said insulation is closed cell foam.

4. The auto-injector system of claim 1 wherein said insulation is closed cell polyurethane foam.

5. The auto-injector system of claim 1 further including a second cavity positioned in said container and a second epinephrine auto-injector positioned in said second cavity.

6. The auto-injector system of claim 1 wherein said auto-injector container top cap includes a cavity adapted to contain said auto-injector top cap.

7. The auto-injector system of claim 1 wherein said auto-injector container top cap includes a tab adapted for rapid opening of said top cap by pulling said tab from action.

8. The auto-injector system of claim 1 said auto-injector container top cap includes thermal insulation positioned in said top cap interior and formed into a cavity in said container top cap.

9. The auto-injector of system of claim 8 wherein the top cap insulation cavity is adapted to contain the auto-injector top cap.

10. The auto-injector system of claim 1 wherein said hinge is a flexible hinge joining said container to said container top cap.

11. The auto-injector system of claim 1 further including a temperature measuring strip positioned inside of said container top cap.

12. The auto-injector system of claim 1 further including a temperature measuring strip positioned inside of said system and adapted to provide an indication of the highest temperature reached inside of the container.

13. The auto-injector system of claim 1 further including a replaceable temperature measuring strip positioned inside of said system.

14. The auto-injector system of claim 1 further including an auto-injector ejector assembly adapted to eject said auto-injector upon opening said container top cap.

15. The auto-injector system of claim 1 further including a bottom flange positioned near the bottom of the container, a spring anchored to said bottom of the container and attached to said bottom flange, whereby upon opening the container top cap the spring and bottom flange cause said auto-injector to pop-up from said container to facilitate grasping of said auto-injector by a user.

16. The auto-injector of claim 1 wherein said container is made of a hard, durable material.

17. The auto-injector system of claim 1 further including a carrying structure, selected from the group consisting of belt clips, loops for shoulder straps, clips, fasteners or other mounting structures adapted for facilitating the carrying of the auto-injector system by a user.

* * * * *